United States Patent [19]
Kimer et al.

[11] Patent Number: 6,127,334
[45] Date of Patent: *Oct. 3, 2000

[54] METHODS FOR PRODUCING BIPHASIC INSULIN FORMULATIONS

[75] Inventors: Lone Løgstrup Kimer, Farum; Per Balschmidt, Espergærde; Steen Jensen, Dragør, all of Denmark

[73] Assignee: Novo Nordisk A/S, Bagsvaerd, Denmark

[ * ] Notice: This patent is subject to a terminal disclaimer.

[21] Appl. No.: 09/198,878

[22] Filed: Nov. 24, 1998

Related U.S. Application Data

[62] Division of application No. 08/879,691, Jun. 19, 1997, Pat. No. 5,948,751.
[60] Provisional application No. 60/023,264, Jun. 26, 1996, and provisional application No. 60/024,862, Aug. 28, 1996.

[30] Foreign Application Priority Data

Jun. 20, 1996 [DK] Denmark ................... 684/96
Aug. 27, 1996 [DK] Denmark ................... 899/96

[51] Int. Cl.[7] .................... A61K 38/28; A61K 31/70; A61K 31/715
[52] U.S. Cl. .................... 514/3; 514/4; 514/53; 514/61; 514/866
[58] Field of Search .............. 514/3, 4, 53, 61, 514/866

[56] References Cited

U.S. PATENT DOCUMENTS

| | | | |
|---|---|---|---|
| 4,439,181 | 3/1984 | Blackshear et al. | 604/56 |
| 4,839,341 | 6/1989 | Massey et al. | 514/4 |
| 4,876,241 | 10/1989 | Feldman et al. | 514/2 |
| 5,053,389 | 10/1991 | Balschmidt et al. | 514/4 |
| 5,149,777 | 9/1992 | Hansen et al. | 530/303 |
| 5,164,366 | 11/1992 | Balschmidt et al. | 514/3 |
| 5,430,016 | 7/1995 | Balschmidt et al. | 514/4 |
| 5,514,646 | 5/1996 | Chance et al. | 514/3 |
| 5,552,385 | 9/1996 | Christensen et al. | 514/18 |
| 5,631,347 | 5/1997 | Baker et al. | 530/303 |
| 5,693,609 | 12/1997 | Baker et al. | 514/3 |
| 5,705,482 | 1/1998 | Christensen et al. | 514/12 |

FOREIGN PATENT DOCUMENTS

| | | |
|---|---|---|
| 0 797 999 A2 | 1/1997 | European Pat. Off. . |
| 94151 | 3/1988 | Romania . |
| 1629023 | 2/1991 | U.S.S.R. . |
| WO 95/00550 | 1/1995 | WIPO . |

OTHER PUBLICATIONS

Pharmaceutical Dosage Forms and Drug Delivery Systems, edited by Ansel et al., publ. by Williams and Wilkins, pp. 317–322, Jan. 1995.
Brange et al., "Chemical Stability of Insulin. 1. Hydrolytic Degradation During Storage of Pharmaceutical Preparations", *Pharmaceutical Research*, vol. 9(6): 715–726, (1992).
Brange et al., "Chemical Stability of Insulin. 2. Formation of Higher Molecular Weight Transformation Products During Storage of Pharmaceutical Preparations", *Pharmaceutical Research*, vol. 9(6): 727–734, (1992).
Brange et al., "Chemical Stability of Insulin. 3. Influence of excipients, formulation, and pH", *Acta. Pharm. Nord.*, vol. 4(3): 149–158, (1992).
Kim et al., "Precipitation of Insulintropin in the Presence of Protamine: Effect of Phenol and Zinc on the Isophane Ratio and the Insulinotropin Concentration in the Supernatant", *Pharmaceutical Research*, vol. 12(9): 1284–1288, (1995).
Gupta and Bhat "Effect of solvent additives on the thermal stability of insulin" (Center for Biotechnology, New Delhi pp. 209–212.

*Primary Examiner*—Howard C. Lee
*Attorney, Agent, or Firm*—Steve T. Zelson, Esq.; Elias J. Lambiris, Esq.

[57] ABSTRACT

Insulin preparations of superior physical stability, comprising dissolved and/or precipitated human insulin or an analogue or derivative thereof, and a water-soluble reduced or non-reducing carbohydrate containing at least 4 carbon atoms in the main carbohydrate structure, or a water-soluble non-reducing ester and/or ether derivative of a carbohydrate or reduced carbohydrate containing at least 4 carbon atoms in the main carbohydrate structure, or mixtures thereof are disclosed.

23 Claims, 3 Drawing Sheets

FIG.1

FIG. 2

# METHODS FOR PRODUCING BIPHASIC INSULIN FORMULATIONS

This application is a divisional of U.S. patent application Ser. No. 08/879,691, filed Jun. 19, 1997, now U.S. Pat. No. 5,948,751 which claims priority under 35 U.S.C. 119 of U.S. Provisional applications 60/023,264 filed Jun. 26, 1996 and 60/024,862 filed Aug. 28, 1996, and of Danish applications 684/96 filed Jun. 20, 1996 and 899/96 filed Aug. 27, 1996, the contents of which are filly incorporated herein by reference.

Introduction

The present invention relates to aqueous insulin preparations comprising human insulin or an analogue or derivative thereof, which preparations have superior physical stability. The invention furthermore relates to parenteral formulations comprising such insulin preparations and to a method for improving the physical stability of insulin preparations.

BACKGROUND OF THE INVENTION

1. Field of the Invention

Diabetes is a general term for disorders in man having excessive urine excretion as in diabetes mellitus and diabetes insipidus. Diabetes mellitus is a metabolic disorder in which the ability to utilize glucose is more or less completely lost. About 2% of all people suffer from diabetes.

Since the introduction of insulin in the 1920's, continuous strides have been made to improve the treatment of diabetes mellitus. To help avoid extreme glycemia levels, diabetic patients often practice multiple injection therapy, whereby insulin is administered with each meal.

In the treatment of diabetes mellitus, many varieties of insulin preparations have been suggested and used, such as regular insulin, Semilente® insulin, isophane insulin, insulin zinc suspensions, protamine zinc insulin, and Ultralente® insulin. As diabetic patients are treated with insulin for several decades, there is a major need for safe and life quality improving insulin preparations. Some of the commercial available insulin preparations are characterized by a fast onset of action and other preparations have a relatively slow onset but show a more or less prolonged action. Fast acting insulin preparations are usually solutions of insulin, while retarded acting insulin preparations can be suspensions containing insulin in crystalline and/or amorphous form precipitated by addition of zinc salts alone or by addition of protamine or by a combination of both. In addition, some patients are using preparations having both a fast onset of action and a more prolonged action. Such a preparation may be an insulin solution wherein protamine insulin crystals are suspended. Some patients do themselves prepare the final preparation by mixing an insulin solution with a suspension preparation in the ratio desired by the patient in question.

Normally, insulin preparations are administered by subcutaneous injection. What is important for the patient, is the action profile of the insulin preparation which is the action of insulin on the glucose metabolism as a function of the time from the injection. In this profile, inter alia, the time for the onset, the maximum value and the total duration of action are important. A variety of insulin preparations with different action profiles are desired and requested by the patients. One patient may, on the same day, use insulin preparations with very different action profiles. The action profile requested is, for example, depending on the time of the day and the amount and composition of any meal eaten by the patient Equally important, however, is the physical stability of the insulin preparations due to the abundant use of pen-like injection devices such as devices which contain Penfill® cartridges, in which an insulin preparation is stored until the entire cartridge is empty. This may last for at least 1 to 2 weeks for devices containing 1.5–3.0 ml cartridges.

2. Description of the Background Art

The first stable neutral insulin suspension was developed by Scott and Fischer (J. Pharmacol. Exp. The. 58 (1936), 78) who discovered that the presence of a surplus of protamine and a zinc salt (2 $\mu$g zinc per IU (international Unit) insulin) could stabilize the protamine insulin preparation, described by Hagedom et al.: J.Am.Med.Assn. 106 (l936), 177–180.

Protamine Zinc Insulin made according to the United States or European Pharmacopoeias contains amorphous protamine zinc insulin as well as crystalline Protamine Zinc Insulin. Freshly prepared protamine zinc insulin contains mainly amorphous precipitate which will partly be transformed into crystalline particles upon storage, leading to a more protracted effect.

A completely crystalline protamine zinc insulin modification designated NPH insulin or Isophane Insulin was developed by Krayenbuhl and Rosenberg (see Rep. Steno Mem. Hosp. Nord. Insulinlab. 1 (1946), 60; and Danish patent No. 64,708). They found that insulin and protamine brought together in isophane proportions at a neutral pH value in the presence of a small amount of zinc and phenol, or phenol derivatives or, preferably m-cresol, will form an amorphous precipitate which upon standing is gradually but completely transformed into oblong tetragonal crystals limited at the ends by pyramidal faces. Insulin and salmon protamine co-crystallize in a weight ratio corresponding to about 0.09 mg protamine sulphate per mg insulin. Zinc in an amount of at least 0.15 $\mu$g per IU and a phenolic in a concentration higher than 0.1% is necessary for the preparation of the tetragonal crystals.

In the early days, this kind of crystals were prepared using, porcine and bovine insulin from natural sources, but from the eighties also human insulin, made by genetic engineering or by semisynthesis, is used.

Human insulin consists of two polypeptide chains, the so-alled A and B chains which contain 21 and 30 amino acids, respectively. The A and B chains are interconnected by two cystine disulphide bridges. Insulin from most other species has a similar construction, but may not contain the same amino acids at the positions corresponding in the chains as in human insulin.

The development of the process known as genetic engineering has made it possible easily to prepare a great variety of insulin compounds being analogous to human insulin. In these insulin analogues, one or more of the amino acids have been substituted with other amino acids which can be coded for by the nucleotide sequences. As human insulin, as explained above, contains 51 amino acid residues, it is obvious that a large number of insulin analogues is possible and, in fact, a great variety of analogues with interesting properties have been prepared. In human insulin solutions with a concentration of interest for injection preparations, the insulin molecule is present in associated form as a hexamer (Brange et al. Diabetes Care 13, (1990), 923–954). After subcutaneous injection, it is believed that the rate of absorption by the blood stream is dependent of the size of the molecule, and it has been found that insulin analogues with amino acid substitutions which counteract or inhibit this hexamer formation have an unusual fast onset of action (Brange et al.: Ibid). This is of great therapeutic value for the diabetic patient. In the crystals of the prolonged acting protamine insulin preparations, the insulin is also found to be hexameric (Balschmidt et al.: Acta Chryst. B47, (1991), 975–986).

Pharmaceutical preparations which are based on analogues of human insulin are e.g. known from the following documents:

WO 95/00550 is concerned with pharmaceutical preparations based on insulin crystals comprising $Asp^{B28}$ insulin and protamine, which display rapid onset and prolonged activity when administered in vivo. The crystals may furthermore contains zinc ions and phenol and/or m-cresol. Glycerol is added to the preparations as isotonicity agent.

In U.S. Pat. No. 5,461,031 various parenteral pharmaceutical formulations, which comprise a rapid-acting monomeric insulin analogue, zinc, protamine and a phenolic derivative, is disclosed. The formulations furthermore contain glycerol which acts as an isotonicity agent.

U.S. Pat. No. 5,474,978 discloses a rapid acting parenteral formulation comprising a human insulin analogue hexamer complex consisting of six monomeric insulin analogues, zinc ions and at least three molecules of a phenolic derivative. The preferred isotonicity agent is glycerol.

Unfortunately, insulin tends to form insoluble and biologically inactive fibrils by non-covalent polymerization (c.f. e.g. Jens Brange, Galenics of Insulin, Springer-Verlag, 1987 and references therein). Fibril formation is promoted by elevated temperatures, e.g. above 30° C., and concomitant movements. This fibrillation process, which is very difficult to avoid, poses an upper limit on the period for which the insulin preparation can be stored and, hence, on the cartridge volume of Penfills®.

Since the formation of fibrils generally requires a monomerization of insulin, insulin analogues which more reluctantly form di- and hexamers, result in preparations of less physical stability due to fibrillation.

Thus, it is an object of the present invention to provide an insulin preparation comprising human insulin or an analogue or derivative thereof with improved physical stability.

According to the invention this object has been accomplished by an aqueous insulin preparation comprising dissolved and/or precipitated human insulin or an analogue or derivative thereof, and a water-soluble reduced or non-reducing carbohydrate containing at least 4 carbon atoms in the main carbohydrate structure, or a water-soluble non-reducing ester and/or ether derivative of a carbohydrate or reduced carbohydrate containing at least 4 carbon atoms in the main carbohydrate structure, or mixtures thereof

DESCRIPTION OF THE INVENTION

Definitions

Figure 1:
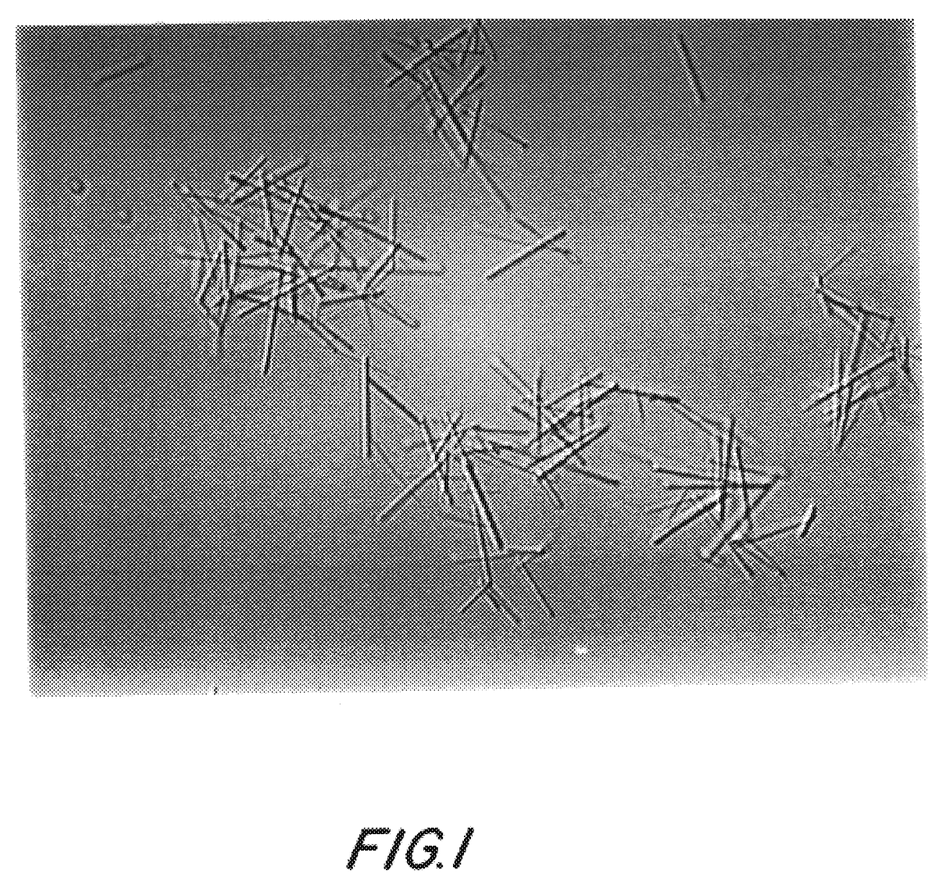
FIG. 1 is a photomicrograph (×1000 magnification) of a formulation of the invention comprising $Asp^{B28}$ human insulin-protamine crystals and mannitol.
Figure 2:
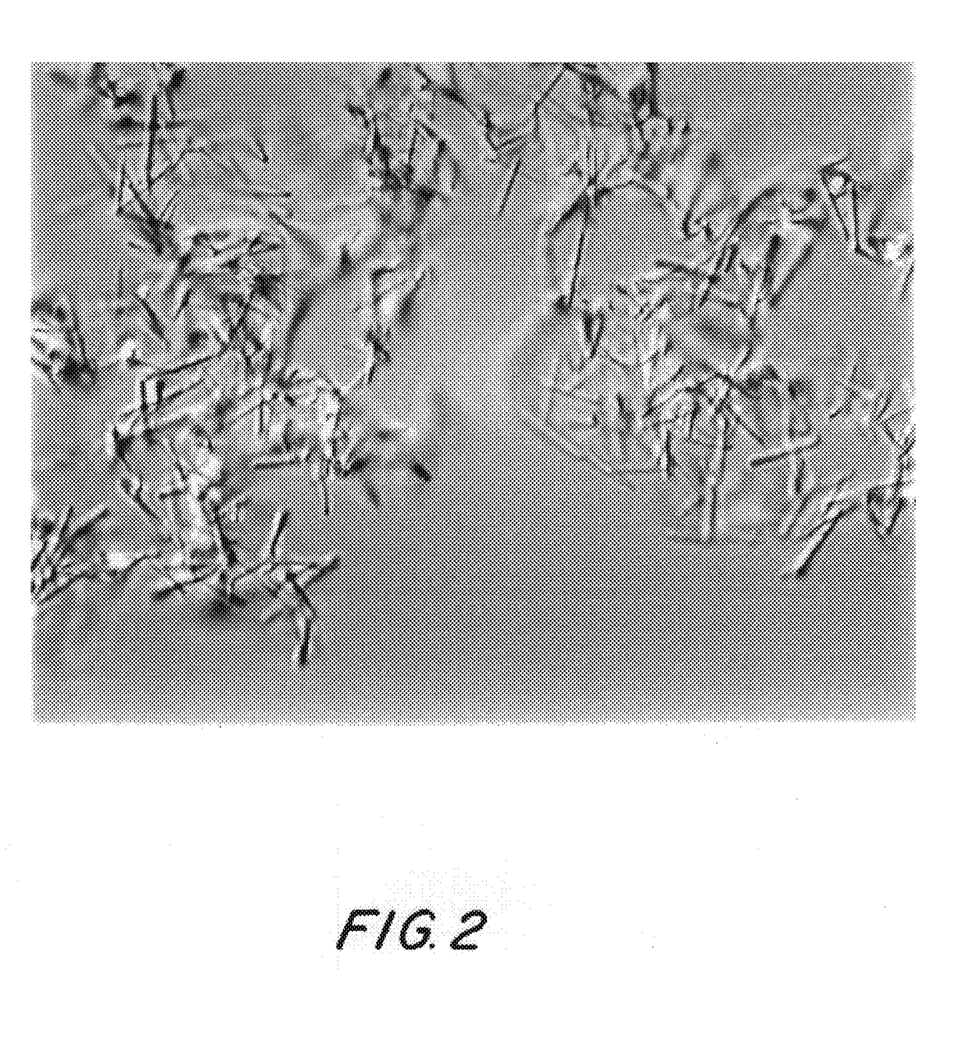
FIG. 2 is a photomicrograph (×1000 magnification) of a formulation of the invention comprising human insulin-protamine crystals and mannitol.
Figure 3:
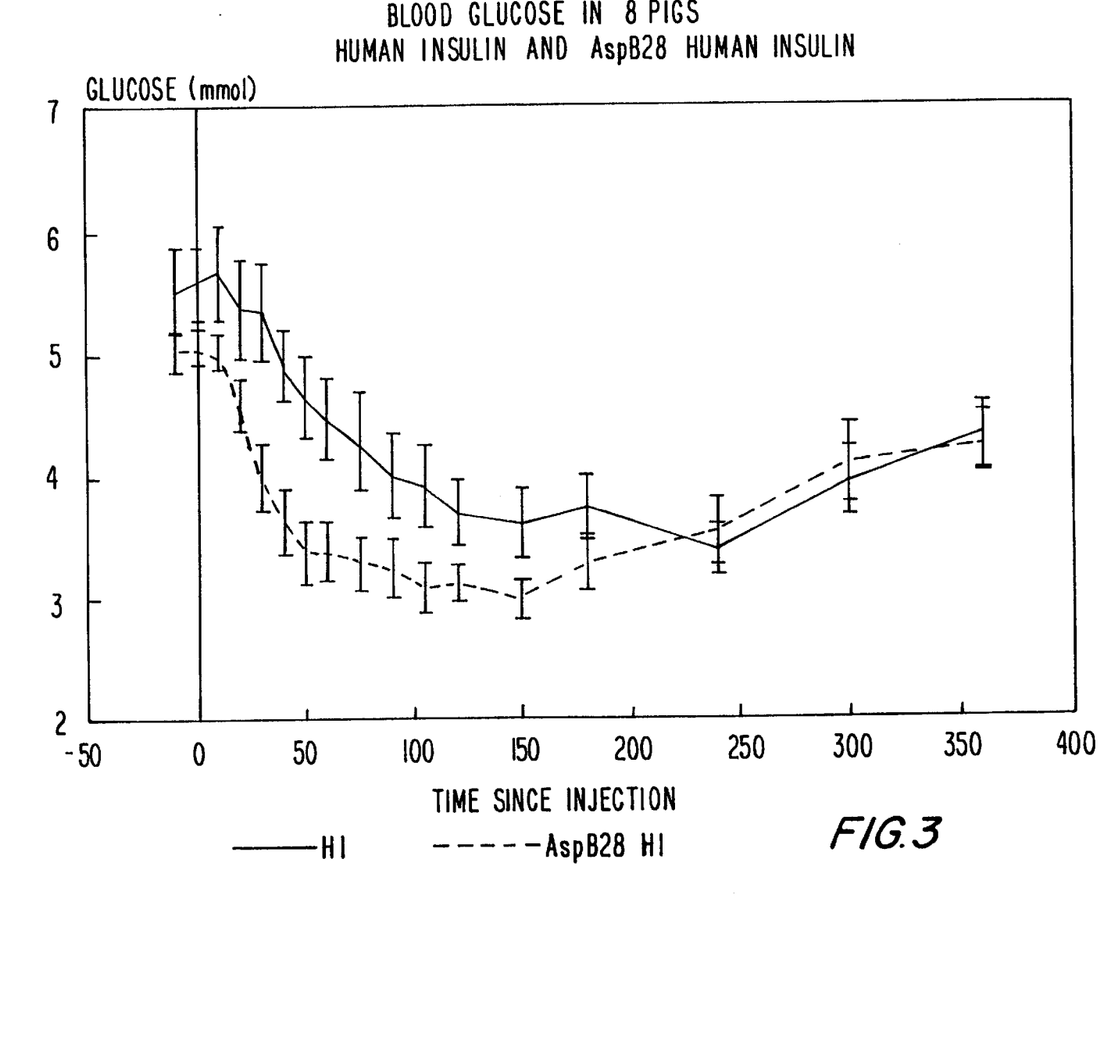
FIG. 3 is a graphical representation of the profile of action of a preparation of the invention containing both dissolved and crystalline $Asp^{B28}$ human insulin and a preparation containing both dissolved and crystalline human insulin. Both preparations furthermore contain mannitol. The graph is the blood glucose response after injection in pigs. The figure demonstrate that the rapid onset of action is preserved for the highly stable $Asp^{B28}$ human insulin preparation.

By "analogue of human insulin" as used herein is meant human insulin in which one or more amino acids have been deleted and/or replaced by other amino acids, including non-codeable amino acids, or human insulin comprising additional amino acids, i.e. more than 51 amino acids.

By "derivative of human insulin" as used herein is meant human insulin or an analogue thereof in which at least one organic substituent is bound to one or more of the amino acids.

In the present context the term "water-soluble" corresponds to a solubility in water of at least about 10 mmol/l, preferably at least 50 mmol/l, at a temperature of 20° C.

The terms carbohydrate, reduced carbohydrate, monosaccharide, disaccharide, and ester and ether derivatives of such compounds are used in accordance with the teaching of K. A. Jensen in "Grundrids af den organiske kemi; Almen Kemi III, 1. Ed., Jul. Gjellerups forlag, 1969, pp. 299–316.

In the present context the expression "non-reducing carbohydrate" denotes a carbohydrate which essentially is incapable of reacting with the amino groups of insulin in the preparations of the invention to form glycated insulin. This definition includes carbohydrates in which the carbonyl group(s) has/have been inactivated or blocked, e.g. by anhydride formation or derivatization.

In one aspect, the present invention relates to an aqueous insulin preparation comprising:

dissolved and/or precipitated human insulin or an analogue and/or a derivative thereof, and 100 to 400 mM, preferably 150 to 250 mM, more preferably 180 to 230 mM, of a water-soluble reduced or non-reducing carbohydrate containing at least 4 carbon atoms in the main carbohydrate structure, or a water-soluble non-reducing ester and/or ether derivative of a carbohydrate or reduced carbohydrate containing at least 4 carbon atoms in the main carbohydrate structure, or mixtures thereof.

In another aspect, the present invention relates to an aqueous insulin preparation comprising:

dissolved and precipitated human insulin or an analogue and/or a derivative thereof, and a water-soluble reduced or non-reducing carbohydrate containing at least 4 carbon atoms in the main carbohydrate structure, or a water-soluble non-reducing ester and/or ether derivative of a carbohydrate or reduced carbohydrate containing at least 4 carbon atoms in the main carbohydrate structure, or mixtures thereof.

In yet another aspect, the present invention relates to an aqueous insulin analogue preparation comprising:

a dissolved and/or precipitated analogue of human insulin, and a water-soluble reduced or non-reducing carbohydrate containing at least 4 carbon atoms in the main carbohydrate structure, or a water-soluble non-reducing ester and/or ether derivative of a carbohydrate or reduced carbohydrate containing at least 4 carbon atoms in the main carbohydrate structure, or mixtures thereof Preferred Embodiments The carbohydrate or carbohydrate derivative used in the insulin preparation of the invention advantageously contains from 5 to 18 carbon atoms in the main carbohydrate structure and is preferably selected from the following compounds:

i) monosaccharides selected from the group of non-reducing aldoses or ketoses, preferably non-reducing aldotetroses, ketotetroses, aldopentoses, ketopentoses, aldohexoses and ketohexoses, more preferably non-reducing aldopentoses, ketopentoses, aldohexoses and ketohexoses;

ii) reduced monosaccharides, i.e. polyhydric alcohols such as alditols, preferably selected from the group consisting of the reduced forms of aldotetroses, ketotetroses, aldopentoses, ketopentoses, aldohexoses and ketohexoses, more preferably of the reduced forms of aldopentoses, ketopentoses, aldohexoses and ketohexoses (i.e. pentitols and hexitols);

iii) non-reducing disaccharides, preferably selected from the non-reducing dihexoses.

Specific examples of suitable reduced or non-reducing carbohydrates are: mannitol, sorbitol, xylitol, inositol, sucrose and trehalose.

The preferred compounds i) to iii) are mannitol and sorbitol, the most preferred being manirtol.

The preferred ester and ether derivatives are $C_1-C_4$ fatty acid ester derivatives and $C_1-C_4$ alkyl ether derivatives, respectively.

In a particular embodiment of the invention, the insulin preparation flirther comprises a halogenide, preferably a chloride, more preferably sodium chloride. It has been shown that the presence of a halogenide results in preparations having an even higher physical stability.

Since insulin preparations comprising fast-acting analogues of human insulin generally show a rather low physical stability, the present invention is particularly advantageous in connection with preparations comprising such analogues. Thus, the insulin preparation according to the invention preferably comprises one or more fast-acting analogues of human insulin, in particular analogues wherein position B28 is Asp, Lys, Leu, Val or Ala and position B29 is Lys or Pro; or des(B28–B30), des(B27) or des(B30) human insulin. The insulin analogue is preferably selected from analogues of human insulin wherein position B28 is Asp or Lys, and position B29 is Lys or Pro. The most preferred analogues are Asp8 human insulin or $Lys^{B28}Pro^{B29}$ human insulin.

In another embodiment the insulin preparation according to the invention comprises an insulin derivative having a protracted profile of action such as insulins having one or more lipophilic substituents. The preferred lipophilic insulins are acylated insulins, including those described in WO 95/07931 (Novo Nordisk A/S), e.g. human insulin derivatives wherein the ε-amino group of $Lys^{B29}$ contains an acyl substituent which comprises at least 6 carbon atoms.

The preferred insulin derivatives are the following:
B29-N$^\epsilon$-myristoyl-des(B30)-human insulin, B29-N$^\epsilon$-myristoyl human insulin, B29-N$^\epsilon$-palmitoyl human insulin, B28-N$^\epsilon$-myristoyl $Lys^{B28}$ $Pro^{B29}$ human insulin, B28-N$^\epsilon$-palmitoyl $Lys^{B28}$ $Pro^{B29}$ human insulin, B30-N$^\epsilon$-myistoyl-$Thr^{B29}$-$Lys^{B30}$ human insulin, B30-N$^\epsilon$-palmitoy-$Thr^{B29}Lys^{B30}$-human insulin, B29-N$^\epsilon$-(N-palmitoyl-γ-glutamyl)-des(B30)-human insulin, B29-N$^\epsilon$-(N-lithocholyl-γ-glutamyl)-des(B30)-human insulin and B29-N$^\epsilon$-(ω-carboxyheptadecanoyl)-des(B30)-human insulin; the most preferred being B29-N$^\epsilon$-myristoyl-des(B30)-human insulin.

In a preferred embodiment the insulin preparation comprises both dissolved and precipitated, preferably crystalline, insulin or insulin analogue or derivative in a weight ratio of 1:99 to 99:1, preferably 20:80 to 80:20, more preferably 30:70 to 70:30.

In this embodiment of the invention, the insulin preparation advantageously comprises crystals comprising: insulin or insulin analogue and protamine, and optionally zinc and/or a phenolic compound, such as phenol, m-cresol or a mixture thereof. The amount of protamine in the crystals preferably corresponds to 0.20 to 0.40 mg protamine base/ 100 IU insulin or insulin analogue. The ratio of protamine to insulin in the crystals more preferably corresponds to the isophane ratio. Zinc is preferably present in an amount of 10 to 40 μg Zn/100 IU insulin, more preferably 15 to 35 μg Zn/100 IU insulin. Phenol and m-cresol, respectively, is preferably present in an amount corresponding to 0 to 4 mg/ml. However, a mixture of 1.4 to 2.0 mg/ml m-cresol and 0.6 to 2.0 mg/ml phenol is most preferred.

A preferred insulin preparation of the invention comprises:
a) 60 to 3000 nmol/mi, preferably 240 to 1200 nmol/ml, of human insulin or insulin analogue and/or insulin derivative;
b) a reduced or non-reducing carbohydrate, preferably mannitol, in a concentration of 100 to 400 mM, preferably 150 to 250 mM, more preferably 180 to 230 mnM;
c) a chloride, preferably sodium chloride, in a concentration of 0 to 100 m preferably 5 to 40 mM, more preferably 5 to 20 mnM; and
d) a physiologically tolerated buffer, preferably a phosphate buffer such as disodiumphosphatedihydrate in an amount of 1 to 4 mg/ml.

The preparation of the invention may flirthermore contain one or more compounds commonly used as isotonicity agents, such as glycerol.

The pH value of the insulin preparation is preferably in the range 7.0 to 7.8.

The present invention is furthermore concerned with a method for preparing an insulin preparation containing both dissolved and precipitated insulin analogue, which method comprises the following steps:
a) providing an acidic solution comprising an analogue of human insulin, zinc, and a sub-isophanic amount of protamine;
b) providing an alkaline solution comprising a substance which acts as a buffer at physiological pH;
wherein at least one of the above solutions further comprises a phenolic compound;
c) mixing the acidic and alkaline solutions and, optionally, adjusting the pH to a value in the range of 6.5 to 8.0, preferably 7.0 to 7.8; and
d) leaving the resulting suspension for precipitation.

By this method an insulin preparation containing both dissolved and precipitated insulin analogue can be obtained in a very simple manner. Furthermore, the precipitate of the resulting suspension usually consists of rod-shaped crystals, which are advantageous in so-called PreMix insulin preparations.

The weight ratio of insulin analogue to protamine in the solution of step a) is preferably selected so as to obtain in the final product a weight ratio of dissolved to precipitated insulin analogue in the range of 1:99 to 99:1, preferably 20:80 to 80:20, more preferably 30:70 to 70:30. More specifically, the solution of step a) preferably comprises 120 to 6000 nmol/ml of insulin analogue and 0.01 to 5.0 mg/ml of protamine.

The solution of step a) further comprises zinc, preferably in an amount corresponding to 10–40 ug zinc/100 IU insulin, more preferably 15–35 ug zinc/100 IU insulin.

In a preferred embodiment, solution a) and/or solution b) comprises chloride, preferably sodium chloride, in an amount corresponding to 0 to 100 mM, preferably 5 to 40 mM, more preferably 5 to 20 mM, in the final product.

The pH of the acidic solution of step a) is preferably below 5, more preferably in the range of 2to3.5.

The insulin analogue is preferably human insulin wherein position B28 is Asp, Lys,. Leu, Val or Ala and position B29 is Lys or Pro; or des(B28–B30), des(B27) or des(B30) human insulin, more preferably $Asp^{B28}$ human insulin or $Lys^{B28}Pro^{B29}$ human insulin, still more preferably $Asp^{B28}$ human insulin.

The phenolic compound used in the solution of step a) and/or step b) is preferably phenol, m-cresol or a mixture thereof.

Advantageously, the solution of step a) and/or step b) fiurther comprises a water-soluble reduced or non-reducing carbohydrate containing at least 4 carbon atoms in the main carbohydrate structure, or a water-soluble non-reducing ester and/or ether derivative of a carbohydrate or reduced carbohydrate containing at least 4 carbon atoms in the main carbohydrate structure, or mixtures thereof.

Said carbohydrate or carbohydrate derivative preferably contains from 5 to 18 carbon atoms in the main carbohydrate structure.

In a particular preferred embodiment, the solution of step a) and/or step b) comprises mannitol, sorbitol, xylitol, inositol, trehalose, sucrose or any mixture thereof, preferably mannitol and/or sorbitol, more preferably mannitol.

The buffer substance employed in the alkaline solution of step b) is preferably a physiologically tolerated buffer, preferably a phosphate buffer, more preferably disodium phosphate dihydrate.

The precipitated insulin analogue is preferably in the form of crystals comprising insulin analogue and protamine.

The suspension obtained in step d) is preferably left at a temperature in the range of 5° C. to 40° C., more preferably 20° C. to 36° C., still more preferably 30° C. to 34° C., for precipitation.

This invention is further illustrated by the following examples which, however, are not to be construed as limiting.

EXAMPLE 1

Preparation 1

An insulin preparation containing both dissolved and crystalline $Asp^{B28}$ human insulin was prepared in the following way:

Solution A:

A solution of $Asp^{B28}$ human insulin at 200 IU/ml concentration was prepared by dissolving 76.5 mg of $Asp^{B28}$ human insulin in water by adding to it 326 µl 0.2 N hydrochloric Acid and 163 µl zinc chloride solution (0.4 mg/ml). Then 6.35 mg protamine sulphate in solution was added to the insulin solution while mixing, and a mixture consisting of 17.2 mg m-cresol, 15 mg phenol and 455 mg mannitol was added to this solution while mixing. The pH of the resulting clear solution was measured to pH=2.6–2.9, and water ad 10 ml was added. The solution was equilibrated at 28–32° C.

Solution B:

25 mg disodium phosphate dihydrate was dissolved in Water for Injection. 17.2 mg m-cresol, 15 mg phenol and 455 mg mannitol was added during mixing. The pH of the resulting clear solution was measured to 9, and water ad 10 ml was added. The solution was equilibrated at 28–320C.

Mixing of solution A and B:

Solution 1 was added to solution A, and the pH was readjusted to 7.30. The resulting suspension was left at 30° C. for 6 days for crystallisation.

In the resulting preparation, the weight ratio of precipitated to dissolved insulin was 70:30.

The preparation was introduced into 1.5 ml Penfill® cartridges.

EXAMPLE II

Preparation 2

An insulin preparation containing both dissolved and crystalline $Asp^{B28}$ human insulin was prepared in the following way:

i) Crystalline Fraction.

Solution A:

A solution of $Asp^{B28}$ human insulin at 200 IU/ml concentration was prepared by dissolving 190.3 mg of $Asp^{B28}$ human insulin in water by adding to it 813 µl 0.2 N hydrochloric acid and 410 µl zinc chloride solution (0.4 mg/ml). Then 16.1 mg protamine sulphate in solution was added to the insulin solution while mixing, and a mixture consisting of 43.0 mg m-cresol, 37.5 mg phenol and 909 mg mannitol, and 14.6 mg sodium chloride was added to this solution while mixing. The pH of the resulting clear solution was measured to pH=2.6–2.9, and water ad 22 ml was added. The solution was equilibrated at 32° C.

Solution B:

62.4 mg disodium phosphate dihydrate was dissolved in water. 43.0 mg m-cresol, 37.5 mg phenol, 909 mg mannitol, and 14.6 mg sodium chloride was added during mixing. The pH of the resulting clear solution was measured to 9, and water ad 22 ml was added. The solution was equilibrated at 32° C.

Mixing of Solution A and B:

Solution B was added to solution A, and the pH was readjusted to 7.30, and water ad 50 ml was added. The resulting suspension was left at 32° C. for 4 days for crystallization.

In the resulting preparation, the weight ratio of precipitated to dissolved insulin was 70:30.

The preparation was introduced into 1.5 ml Penfill® cartridges.

EXAMPLES III–VI

Preparations 3 to 6

Insulin preparations containing both dissolved and crystalline $Asp^{B28}$ human insulin was prepared as described in Example II, except that the amount of mannitol used in Solution A and B was 818 mg, 1005 mg, 1047 mg and 1137 mg, respectively.

The preparations were introduced into 1.5 ml Penfill® cartridges.

EXAMPLE VII

Preparation 7

An insulin preparation containing both dissolved and crystalline $Lys^{B28}Pro^{B29}$ human insulin was prepared in the following way:

i) Crystalline Fraction.

Solution A:

A solution of $Lys^{B28}ProB^{29}$ human insulin at 200 IU/ml concentration was prepared by suspending 69.7 mg of $Lys^{B28}Pro^{B29}$ human insulin in water. A mixture consisting of 16.0 mg m-cresol, 6.5 mg phenol, 364 mg mannitol and 25.1 mg disodium diphosphate dihydrate was added to this solution while mixing. Then 50 µl zinc chloride solution (10 mg/ml) was added. The pH of the resulting clear solution was readjusted to 7.40, and water ad 10 ml was added. The solution was equilibrated at 15° C.

Solution B:

A solution of protamine sulphate was prepared by dissolving 7.61 mg protamine sulphate and 25.1 mg disodium phosphate dihydrate in water. 16.0 mg m-cresol, 6.5 mg phenol and 364 mg mannitol was added during mixing. This solution was added to the protamine sulphate solution while mixing. The pH of the resulting clear solution was readjusted to 7.40, and water ad 10 ml was added. The solution was equilibrated at 15° C.

Mixing of Solution A and B:

Solution B was added to solution A, arid the pH was readjusted to 7.30. The resulting suspension was left at 15° C. for 3 days for crystallization.

ii) Dissolved Fraction

A solution of $Lys^{B28}Pro^{B29}$ human insulin was prepared by dissolving 34.9 mg $Lys^{B28}Pro^{B29}$ human insulin in water by adding to it 33 μl 1 N hydrochloric acid and 25 μl zinc chloride solution (10 mg/ml). Then a mixture consisting of 26.1 mg sodium phosphate dihydrate, 6.5 mg phenol, 16.0 mg m-cresol and 364 mg mannitol was added to the insulin solution while mixing. The pH of the resulting clear solution was measured to pH=7.3, and water ad 10 ml was added.

6 ml of the dissolved fraction was added to 14 ml of the crystalline fraction, and the pH was adjusted to 7.30.

In the resulting preparation, the weight ratio of precipitated to dissolved insulin was 70:30.

The preparation was introduced into 1.5 ml Penfill® cartridges.

EXAMPLE VIII

Preparation 8

An insulin preparation containing both dissolved and crystalline human insulin was prepared in the following way:

i) Crystalline Fraction

Solution A:

A solution of human insulin was prepared by dissolving 69.7 mg human insulin in water by adding to it 65 μl 1 N hydrochloric acid and 26 μl zinc chloride solution (10 mgml). Then 6.0 mg protamine sulphate in solution was added to the insulin solution while mixing, and a mixture consisting of 15.0 mg phenol and 17.2 mg m-cresol was added to the solution while mixing. The pH of the resulting clear solution was measured to pH=2.7–3.2, and water ad 10 ml was added.

Solution B:

24.9 mg sodium phosphate dihydrate was dissolved in water. 15 mg phenol, 17.2 mg m-cresol, 728 mg manrnitol and 11.7 mg sodium chloride was added during mixing. The pH of the resulting clear solution was adjusted to pH=9, and water ad 10 ml was added.

Solution B was added to solution A, and the pH was adjusted to 7.30. The resulting suspension was left at 22–24° C. until the next day.

ii) Dissolved Fraction

A solution of human insulin was prepared by dissolving 34.9 mg human insulin in water by adding to it 33 μl 1 N hydrochloric acid and 13 μl zinc chloride solution (10 mg/ml). Then a mixture consisting of 12.5 mg sodium phosphate dihydrate, 15 mg phenol, 17.2 mg m-cresol, 364 mg mannitol and 5.8 mg sodium chloride was added to the insulin solution while mixing. The pH of the resulting clear solution was measured to pH=7.3, and water ad 10 ml was added.

6 ml of the dissolved fraction was added to 14 ml of the crystalline fraction, and the pH was adjusted to 7.30.

In the resulting preparation, the weight ratio of precipitated to dissolved insulin was 70:30.

The preparation was introduced into 1.5 ml Penfill® cartridges.

EXAMPLE IX

Preparation 9

An insulin preparation containing both dissolved and crystalline $ASPB^28$ human insulin was prepared in the following way:

Solution A:

A solution of $Asp^{B28}$ human insulin at 200 IU/ml concentration was prepared by dissolving 189.9 mg of $Asp^{B28}$ human insulin in water by adding to it 163 μl 1 N hydrochloric acid and 163.5 μl zinc chloride solution (10 mg/ml). Then 11.5 mg protamine sulphate in solution was added to the insulin solution while mixing, and a mixture consisting of 44.3 mg m-cresol, 38.6 mg phenol and 1048 mg mannitoll, and 7.3 mg sodium chloride was added to this solution while mixing. The pH of the resulting clear solution was measured to pH=2.6–2.9, and water ad 25 ml was added The solution was equilibrated at 22–24° C.

Solution B:

62.3 mg disodium phosphate dihydrate was dissolved in water. 44.3 mg m-cresol, 38.6 mg phenol, 1048 mg mannitol, and 7.3 mg sodium chloride was added during mixing. The pH of the resulting clear solution was measured to 9, and water ad 25 ml was added. The solution was equilibrated at 22–24° C.

Mixing of Solution A and B:

Solution B was added to solution A, and the pH was readjusted to 7.30. The resulting suspension was left at 32° C. for 2 days for crystallisation.

In the resulting preparation, the weight ratio of precipitated to dissolved insulin was 50:50.

The preparation was introduced into 1.5 ml Penfill® cartridges.

EXAMPLE X (Comparative)

Preparation 10

An insulin preparation containing both dissolved and crystalline $Asp^{B28}$ human insulin was prepared in the following way:

Solution A:

A solution of $Asp^{B28}$ human insulin at 200 IU/ml concentration was prepared by dissolving 76.5 mg of $Asp^{B28}$ human insulin in water by adding to it 326 μl 0.2 N hydrochloric acid and 163 μl zinc chloride solution (0.4 mg/ml). Then 6.35 mg protamine sulphate in solution was added to the insulin solution while mixing, and a mixture consisting of 17.2 mg m-cresol, 15.0 mg phenol and 160 mg glycerol was added to this solution while mixing. The pH of the resulting clear solution was measured to pH=2–6–2.9, and water ad 10 ml was added. The solution was equilibrated at 28–32° C.

Solution B:

25 mg disodium phosphate dihydrate was dissolved in Water for Injection. 17.2 mg m-cresol, 15.0 mg phenol and 160 mg glycerol was added during mixing. The pH of the resulting clear solution was measured to 9, and water ad 10 ml was added. The solution was equilibrated at 28–32° C.

Solution B was added to solution A, and the pH was readjusted to 7.30. The resulting suspension was left at 28–32° C. for 2 days for crystallization.

In the resulting preparation, the weight ratio of precipitated to dissolved insulin was 70:30.

The preparation was introduced into 1.5 ml Penfill® cartridges.

EXAMPLE XI

PHYSICAL STRESS TESTS 5 samples of each insulin preparation were introduced into Penfill® cartridges and subjected to the following physical stress test:

The Penfil® cartridges were fixed to a rotator which were placed in an incubator, and rotated 360° for four hours per day with a frequency of 30 rotations per minute and at a constant temperature of 37° C.±2° C. The Penfill® cartridges were stored at a temperature of 37° C.±2° C., when they were not rotated.

The Penfill® cartridges were inspected macroscopically 5 times a week and changes in the appearance of the formulation were noted according to following principles:21
i) Cartridges containing a white suspension resuspendable on agitation and free of lumps and granules were classified as "not fibrillated".
ii) Cartridges containing a suspension with lumps and/or granules not resuspendable on agitation and/or depositing on the cartridge wall were assumed "fibrillated". This was confirmed by addition of 6 μl 6N HCl to the cartridge: Fibrillated cartridges are not visually clear after addition of acid.

Rotation of the cartridges was continued until all samples were fibrillated.

The results are summarized in the following Table I

TABLE I

| Preparation No | Composition | Average No. of days to fibrillation | First day of fibrillation |
|---|---|---|---|
| 1 | Asp$^{B28}$ insulin 30/70<br>7 mM phosphate<br>250 mM-mannitol | 20 | 20 |
| 2 | Asp$^{B28}$ insulin 30/70<br>7 mM phosphate<br>200 mM mannitol<br>10 mM sodium chloride | 23 | 23 |
| 3 | Asp$^{B28}$ insulin 30/70<br>7 mM phosphate<br>180 mM mannitol<br>10 mM sodium chloride | 21 | 17 |
| 4 | Asp$^{B28}$ insulin 30/70<br>7 mM phosphate<br>220 mM mannitol<br>10 mM sodium chloride | 19 | 17 |
| 5 | Asp$^{B28}$ insulin 30/70<br>7 mM phosphate<br>230 mM mannitol<br>10 mM sodium chloride | 21 | 18 |
| 6 | Asp$^{B28}$ insulin 30/70<br>7 mM phosphate<br>250 mM mannitol<br>10 mM sodium chloride | 22 | 22 |
| 9 | Asp$^{B28}$ insulin 50/50<br>7 mM phosphate<br>230 mM mannitol<br>10 mM sodium chloride | >30 | >30 |
| 10 (Comparative) | Asp$^{B28}$ insulin 30/70<br>7 mM phosphate<br>174 mM glycerol | 11 | 9 |

What is claimed is:

1. A method for preparing an insulin product, comprising the steps of:
   (a) providing an acidic solution comprising an insulin analogue, a source of zinc, and a sub-isophanic amount of protamine, wherein the weight ratio of the insulin analogue to protamine in the acidic solution results in a weight ratio of dissolved to precipitated insulin analogue in the range of 20:80 to 80:20 in the insulin product;
   (b) providing an alkaline solution comprising a substance which acts as a buffer at physiological pH; wherein at least one of the solutions of steps (a) and (b) further comprises a phenolic compound;
   (c) mixing the acidic and alkaline solutions to form a suspension; and
   (d) leaving the suspension to form the insulin product which comprises a soluble phase comprising the insulin analogue and a solid phase comprising the precipitated insulin analogue.

2. The method of claim 1, wherein the weight ratio of the insulin analogue in the final product is between 30:70 to 70:30.

3. The method of claim 1, wherein the source of zinc is zinc chloride.

4. The method of claim 1, wherein the source of zinc is present in an amount corresponding to 10–40 μg zinc/100 IU insulin.

5. The method of claim 4, wherein the source of zinc is present in an amount corresponding to 15–35 μg zinc/100 IU insulin.

6. The method of claim 1, wherein the acidic solution of step (a) and/or the alkaline solution of step (b) further comprises chloride in an amount corresponding to 0 to 100 mM in the final product.

7. The method of claim 6, wherein the chloride is present in an amount corresponding to 5 to 20 mM in the final product.

8. The method of claim 6, wherein the chloride is sodium chloride.

9. The method of claim 1, wherein the pH of the acidic solution of step (a) is below 5.

10. The method of claim 9, wherein the pH of the acidic solution of step (a) is in the range of 2 to 3.5.

11. The method of claim 1, wherein the insulin analogue is selected from the group consisting of: (i) human insulin wherein position B28 is Asp, Lys, Leu, Val or Ala and position B29 is Lys or Pro; (ii) des (B28–B30) human insulin; des(B27) human insulin; and des(B30) human insulin.

12. The method of claim 11, wherein the insulin analogue is Asp$^{B28}$ human insulin.

13. The method of claim 11, wherein the insulin analogue is Lys$^{B28}$Pro$^{B29}$ human insulin.

14. The method of claim 1, wherein the phenolic compound is selected from the group consisting of phenol, m-cresol or a mixture thereof.

15. The method of claim 1, wherein the acidic solution of step (a) and/or the alkaline solution of step (b) further comprises a water-soluble reduced or non-reducing carbohydrate containing at least 4 carbon atoms in the main carbohydrate structure, or a water-soluble non-reducing ester and/or ether derivative of a carbohydrate or reduced carbohydrate containing at least 4 carbon atoms in the main carbohydrate structure, or mixtures thereof.

16. The method of claim 15, wherein the carbohydrate or carbohydrate derivative contains from 5 to 18 carbon atoms in the main carbohydrate structure.

17. The method of claim 16, wherein the carbohydrate or carbohydrate derivative is mannitol, sorbitol, xylitol, trehalose, sucrose or any mixture thereof.

18. The method of claim 1, wherein the buffer substance employed in the alkaline solution of step (b) is a physiologically tolerated buffer.

19. The method of claim 1, wherein the precipitated insulin analogue is in the form of crystals comprising insulin analogue and protamine.

20. The method of claim 1, wherein the suspension obtained in step (c) is left at a temperature in the range of 5° C. to 40° C. for precipitation.

21. The method of claim 1, further comprising adjusting the pH of the mixture of the acidic and alkaline solutions of step (c) to a value in the range of 6.5 to 8.0.

22. The method of claim 21, wherein the pH is adjusted to 7.0 to 7.8.

23. The method of claim 1, wherein the precipitated insulin analogue is in the form of crystals.

* * * * *